(12) United States Patent
Cattaruzzi et al.

(10) Patent No.: US 12,116,561 B2
(45) Date of Patent: *Oct. 15, 2024

(54) AUTOMATED CELL CULTURING AND HARVESTING DEVICE

(71) Applicant: VivaBioCell S.p.A., Udine (IT)

(72) Inventors: Giacomo Cattaruzzi, Fagagna (IT); Massimo Moretti, Povoletto (IT); Antonio Sfiligoj, Duino Aurisina (IT); Francesco Curcio, Pagnacco (IT)

(73) Assignee: VIVABIOCELL S.P.A., Udine (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/447,736

(22) Filed: Aug. 10, 2023

(65) Prior Publication Data
US 2023/0383237 A1 Nov. 30, 2023

Related U.S. Application Data

(63) Continuation of application No. 15/304,587, filed as application No. PCT/EP2015/057610 on Apr. 28, 2015, now Pat. No. 11,773,364.

(30) Foreign Application Priority Data

Apr. 28, 2014 (EP) ..................................... 14166238

(51) Int. Cl.
*C12M 1/00* (2006.01)
*C12M 1/26* (2006.01)
(Continued)

(52) U.S. Cl.
CPC ............ *C12M 41/48* (2013.01); *C12M 23/20* (2013.01); *C12M 23/28* (2013.01); *C12M 27/14* (2013.01);
(Continued)

(58) Field of Classification Search
CPC ...... C12M 23/20; C12M 23/28; C12M 27/14; C12M 27/16; C12M 29/26; C12M 33/04; C12M 33/08; C12M 41/12; C12M 41/48
See application file for complete search history.

(56) References Cited

U.S. PATENT DOCUMENTS

| 2006/0141623 A1 | 6/2006 | Smith et al. |
| 2008/0032398 A1 | 2/2008 | Cannon et al. |

(Continued)

FOREIGN PATENT DOCUMENTS

| EP | 0402272 B1 | 10/1995 |
| WO | 95/04813 A1 | 2/1995 |

(Continued)

OTHER PUBLICATIONS

PCT Notification of Transmittal of the International Search Report and Written Opinion, PCT International Search Report and PCT Written Opinion issued for PCT application No. PCT/EP2015/057610, which was mailed Jul. 3, 2015 (12 pages).

*Primary Examiner* — Lydia Edwards
(74) *Attorney, Agent, or Firm* — Lucas & Mercanti, LLP

(57) ABSTRACT

An automated cell culturing device, which expands, detaches and prepares cells, ready to be implanted in vivo is disclosed. The device is composed by a multi-layered cell culture chamber, a cell preparation chamber, and critical parameters control units which automatically drive the cell culture medium circulation, change and refill. The device according to the invention is characterized in that all the components contacting cells and culture medium constitute a totally disposable "cartridge" in order to avoid cross-contamination and improve safety. The device is particularly useful for expanding and preparing mesenchymal stem cells for osteoarthritis (OA) therapy, and for other cell based therapies in mammals.

19 Claims, 3 Drawing Sheets

(51) Int. Cl.
  *C12M 1/34* (2006.01)
  *C12M 1/36* (2006.01)
  *C12M 3/06* (2006.01)
(52) U.S. Cl.
  CPC ............ *C12M 27/16* (2013.01); *C12M 29/26* (2013.01); *C12M 33/04* (2013.01); *C12M 33/08* (2013.01); *C12M 41/12* (2013.01)

(56) References Cited

U.S. PATENT DOCUMENTS

| | | |
|---|---|---|
| 2008/0220523 A1 | 9/2008 | Antwiler |
| 2008/0227190 A1 | 9/2008 | Antwiler et al. |
| 2009/0191620 A1 | 7/2009 | Martin et al. |
| 2012/0315693 A1 | 12/2012 | Martin et al. |
| 2013/0058907 A1 | 3/2013 | Wojciechowski et al. |
| 2013/0157353 A1 | 6/2013 | Dijkhuizen Borgart et al. |
| 2013/0210130 A1 | 8/2013 | Larcher et al. |
| 2013/0244322 A1 | 9/2013 | Henon et al. |

FOREIGN PATENT DOCUMENTS

| | | |
|---|---|---|
| WO | 03/087292 A2 | 10/2003 |
| WO | 2008/112845 A2 | 9/2008 |
| WO | 2010/048417 A2 | 4/2010 |
| WO | 2011/073261 A2 | 6/2011 |
| WO | 2011/142670 A1 | 11/2011 |

A

B

AUTOMATED CELL CULTURING AND HARVESTING DEVICE

CROSS-REFERENCE TO RELATED APPLICATIONS

This application is a continuation of U.S. patent application Ser. No. 15/304,587, filed Oct. 17, 2016, which in turn is a 371 of PCT/EP2015/057610, filed Apr. 8, 2015, which claims the benefit of European Patent Application No. EP14166238.7 filed Apr. 28, 2014. The disclosure of each of the foregoing applications is incorporated herein by reference.

The present invention relates to a cell culturing and harvesting device for the transplantation or implantation in vivo. More particularly, the present invention relates to a device that ensures fully automated and controlled expansion of a cell culture, and that ensures fully automated and controlled preparation of a cell suspension to be transplanted or implanted in vivo. Cells are cultured as mono-layers. Cells can also be cultured onto three-dimensional (3D) structures or on suitable rafts or beads to increase culture surface.

There is increasing interest in growing cells in three-dimensional (3D) environments such as on a 3D structure or scaffold. Cell culture on 3D scaffolds is useful in tissue engineering for the generation of implantable tissue structures.

WO2011/073261A1 describes a cell processing device (bioreactor) for culturing mammalian cells in adhesion onto a three-dimensional structure for the transplantation or implantation in vivo, comprising a circulation system, a culture device, fluid reservoir and pumps.

EP0402272B1 describes a microorganism or cell culturing substrate consisting of a high molecular substrate coated on at least one of its opposite surfaces by a synthetic high molecular membrane layer made up of a (co)polymer of an α,β-ethylenically unsaturated monomer possessing a nitrogen-containing heterocycle in the molecular unit thereof.

US2013/0058907 describes a cell culture system incorporating a disposable cultureware module and a reusable compact instrumentation base device that is capable of expanding cells including primary cells and cell lines as well as patient-specific cells or cells lines in an automated, contaminant-free manner.

WO2010/048417 describes a perfusion bioreactor, comprising a housing with an inlet port and outlet port, and a cell growth matrix, wherein the cell growth matrix is planar, pleated, or spirally wound around a central core.

US2008/0032398A1 describes an incubator rack for supporting a plurality of cell culture perfusion flowpath assembly cartridges, comprising: a horizontal base having a surface with a plurality of grooves each adapted to support a flowpath assembly cartridge; a plurality of data interface connections for transmitting data between said rack and said plurality of cartridges; and at least one control interface for communication between said rack and an external computer.

US2008/0220523A1 describes a method of expanding cells ex vivo, the method comprising: seeding the cells on a hollow fiber substrate so that the cells adhere to the substrate; expanding the adhered cells on the substrate; removing the expanded cells from the substrate, wherein the cells are non-embryonic stem, non-germ cells, wherein the cells express telomerase, are not transformed, and have a normal karotype.

US2013/0210130A1 describes an automated cell culture arrangement comprising one closed cell culture module comprising one bioreactor, the closed cell culture module being a closed system, and a plurality of tool modules comprising one pump and one additional tool module, wherein at least one of the additional tool module is movable relative to the closed cell culture module or relative to one or several components of the closed cell culture module, and configured or configurable to act upon or monitor the contents of a bioreactor without opening the closed cell culture module or disconnecting the closed cell culture module from the automated cell culture arrangement.

US2013/0244322A1 describes an automated apparatus of cell culture, comprising tanks of culture medium, growth factors and cells to be cultured, an incubator with a thermostated enclosure in which is housed a container for cell culture or expansion, and a control computer system including means for entering and recording data intended to control the culture conditions in the enclosure and to manage valves for dispensing fluids in a predefined sequence, wherein it comprises a device for supporting and agitating the cell culture or expansion container which is controlled by said computer system and which is housed in said enclosure, and wherein said container is formed by a cell expansion bag having at least one inlet port connected to said tanks and one outlet port connected to means of harvesting and storage of the cells after culture, these harvesting and storage means and said tanks being located outside the enclosure and being connected to said ports of said cell expansion bag by conduits which form with said cell expansion bag a preassembled module placed in said enclosure and which pass through a wall of said enclosure so as to allow to feed the cell expansion bag with said culture medium, growth factors and cells to be cultured, and to harvest the contents of said cell expansion bag in the harvesting and storage means while maintaining the enclosure closed.

US2012/0315693A1 describes a cell growth apparatus comprising: a plurality of cell growth chambers, each having a gas permeable, liquid impermeable membrane, an opposing surface, and at least one side wall connected to at least one of the gas permeable, liquid impermeable membrane and the opposing surface; at least one tracheal space in communication with at least one gas permeable, liquid impermeable membrane of at least one cell growth chamber; wherein the at least one tracheal space comprises peripheral supports on a peripheral edge of the tracheal space; wherein the supports on the peripheral edge of the tracheal space are spaced apart to create a plurality of gaps to allow gasses to flow from an external environment into the tracheal space through the plurality of gaps between peripheral supports; and a manifold wherein the manifold provides access at least one of the plurality of cell growth chambers.

US2009191620 describes a multi-layer cell culture device comprising a three cell culture chambers, each cell culture chamber having at least one port, each port having a port cover; two integral tracheal chambers, wherein each port is structured and arranged to engage with a hinged port cover to provide a releasable liquid tight seal.

WO08112845A2 describes a disposable apparatus for cell expansion, having at least one bioreactor having cellular growth area and a supply area, the cellular growth area being adjacent a plate and separated from said supply area by a membrane. The bioreactor comprises a plurality of plates having a roughened surface or a corrugated surface. At least a sheet of membrane separates adjacent plates. Two sheets between adjacent plates may be separated by a mesh.

A problem connected with the cell culturing devices is therefore the contamination due to human manipulation and to the use of the same apparatus for different cell cultures.

There is a need to provide methods for the culture and the preparation of cells to be implanted or transplanted in vivo being highly automated, in order to avoid human manipulation and contaminations and to provide a device which is made of disposable parts in order to prevent cross contamination between different cell lines. We have now found an automated cell culturing and harvesting device, which automatically expands, detaches and prepares cells ready to be implanted in vivo wherein the components contacting cells and culture medium constitute a totally disposable "cartridge" in order to avoid cross-contamination and improve safety. An object of the present invention is therefore an automated cell culturing device, which automatically expands, detaches and prepares cells, ready to be implanted in vivo wherein the components contacting cells and culture medium constitute a totally disposable "cartridge".

All components of the cell culturing and harvesting device according to the present invention contacting with cells and cell culture medium are totally disposable (single-use), in order to completely prevent cross contamination between one culture and another, without the need of washing, or cleaning-in-place, any component of the device.

The cell culturing and harvesting device according to the present invention is composed by a group of components which are not in contact with cells and cell culture medium (valves, pumps, sensors, actuator motors, temperature control systems, non-invasive parameters control sensors). This group of components may constitute the "hardware" part of the device.

The group of components which come in contact with cells and culture medium (tubing system, cell culture chamber, cell preparation chamber, reservoirs, waste tank) may constitute the disposable part of the device, namely a "cartridge system" or "cartridge".

The device object of the present invention is composed preferably by separated compartments adjusted at different temperatures.

Preferably the first compartment, wherein seeding and expansion of cells occur, is subjected to temperature control in order to maintain a temperature of about 37° C. and may include key components of the cell culture, such as the culture chamber and a certain amount of circulating cell culture medium.

Preferably the second compartment is subjected to temperature control in order to maintain a temperature between about 4° C. and about 8° C. and may include a fresh medium reservoir, and a certain amount of cell detaching agent to be used for cell detaching in final phases of operation.

Fresh medium and detaching agent are preferably maintained at low temperatures in order to preserve biological activities of their key components.

Preferably the device according to the present invention is provided with a continuous circulation of medium which ensures the distribution of nutrients inside the cell culture chamber, and for efficient gas exchange in order to maintain pH at about 7. Furthermore medium change (i.e. discharge of exhausted medium and refill with fresh medium) is important for maintaining optimal nutrients concentration, and to reduce catabolites concentration following cell number increase.

The term "nutrients" or "nutrients solution" is intended to include liquid solutions containing those nutrient substances essential to the culture of mammalian or vertebrate cells. Nutrient solutions may also affect specific changes in phenotype of cells under culture. Suitable nutrients which can be used for the present invention are known in the art and may include fetal bovine serum, autologous human serum, L-ascorbid acid, antibiotics, amminoacid supplements, antioxidants, minerals, cell modulators, activators or inhibitors.

In the device object of the present invention, monitoring of nutrients and catabolites concentration allows the automatic execution of medium change, according to the principle, known in the art, that nutrients concentration should never fall under a certain threshold value, and that catabolites concentration should never exceed a certain value.

Preferably the medium change operation includes the input of fresh medium from the second compartment of the device object of the present invention, and medium discharge to a waste tank.

In the case of cultivating cells which adhere and grow onto a surface, homogeneous cell seeding inside a cell culture chamber is a frequent problem in automated devices. In order to ensure appropriate distribution of cells to be seeded, the cell culture chamber of the device object of the present invention is preferably designed including several growth surfaces (layers) and empty spaces between layers and external shell. During seeding phase operation in the device object og the present invention, rotation of cell culture chamber and the presence of empty spaces, may ensure homogeneous distribution of cells onto the seeding surfaces.

Another problem in automated cell culture devices known in the art is cell detaching and harvesting.

Another object of the present invention is to provide an automated cell culturing device which is also able to automatically detach adherent cells and prepare them for implantation into the body.

The present device is characterized by automated administration of a detaching agent, together with rotation and vibration of cell culture chamber during the cell detaching phase which ensures efficient and homogeneous cell harvesting.

In the cell preparation chamber, cells are concentrated while detaching agent is discarded.

The cell culture chamber is preferably composed by any bio-compatible material preferably the external shell and the deflectors are selected among polystyrene (PS), polycarbonate (PC), polyoxy-methylene and internal layers are composed by polystyrene (PS), eventually treated for cell adhesion enhancement.

Preferably the treatments for cell adhesion comprise oxygen plasma surface treatment, poly-D-lysine treatment, active peptide acrylates treatment. Alternatively, layers may be coated with substances suitable for subsequent cell detaching.

Preferably layers are coated with alginate gel with or without the addition of adhesion focal plaques components (RGD) or cell-surface adhesion molecules.

Cell preparation chamber is preferably connected to a syringe or other extraction devices known in the art for immediate collection of cells ("output cells"). "Output cells" refer to the cells harvested from the device after having been expanded in the device. Output cells are preferably used in the clinic or for other purposes, such as research, clinical trials, and the like.

The whole operations do not include the contact of cells or cell culture medium with the external environment, thus preventing contamination possibility. Moreover, operations are totally controlled by automatic actuators, thus preventing possible human errors.

Preferred types of cells to be seeded, expanded, prepared and harvested in the present device include, but are not limited to, non-embryonic stem non-germ cells prepared from any desirable tissue, including, but not limited to, bone marrow, adipose tissue, umbilical cord blood, umbilical cord matrix, peripheral blood, placenta, placental blood, muscle, brain, kidney and other solid organs or excreted fluids.

Preferably cells to be seeded, expanded, prepared and harvested in the device object of the present invention are cells which can live and proliferate in adhesion in-vitro, more preferably adipose-derived mesenchymal stem cells (AD-MSC), bone marrow derived mesenchymal stem cells (BMSC).

Preferred uses of the device object of the present invention are the expansion of mesenchymal stem cells for in vivo cell therapy in all applications where adhesion-dependent cells are needed in suspension, to be injected such as in osteoarthritis (OA) (also known as degenerative arthritis or degenerative joint disease or osteoarthrosis) treatment or other diseases in which immunemodulation and/or tissue repair are needed.

Another object of the present invention is therefore the use of the automated cell culturing device for expanding and preparing mesenchymal stem cells for in vivo cell therapy in mammals, preferably for all applications where adhesion-dependent cells are needed in suspension to be injected, more preferably for the production of cells for the treatment of osteoarthritis or other diseases in which immunomodulation and/or tissue repair are needed.

DETAILED DESCRIPTION OF THE DRAWINGS

Figure 1:
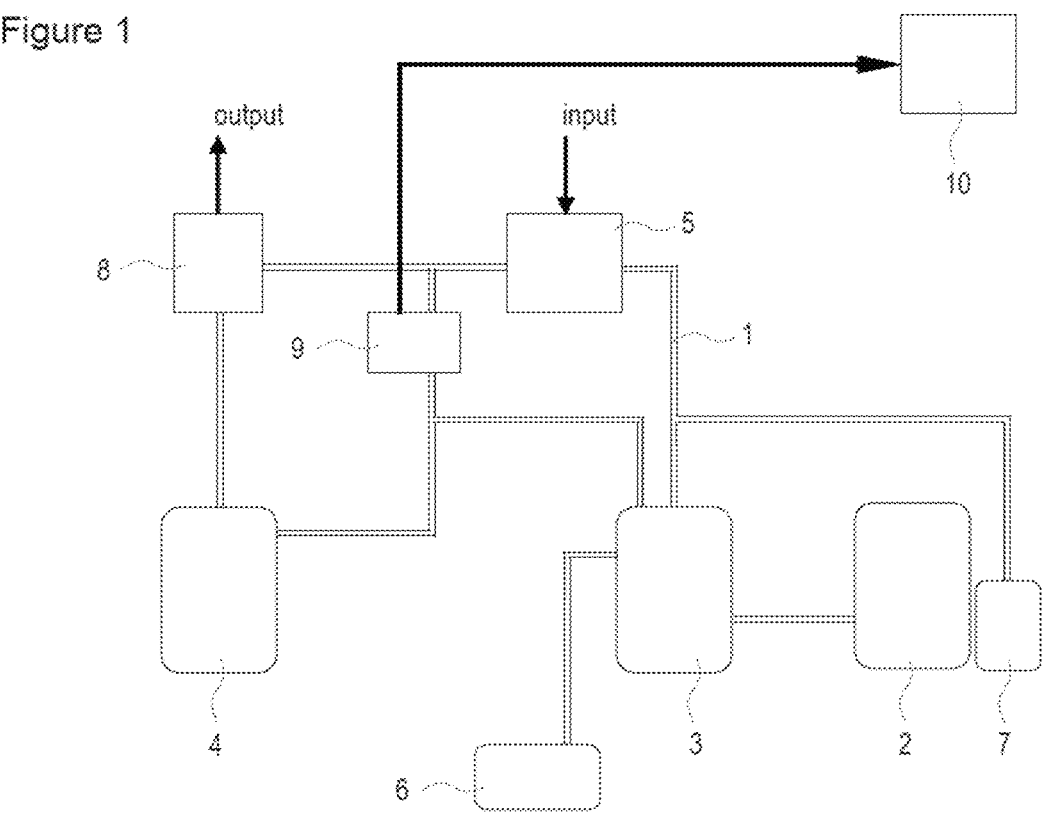
FIG. 1 represents an overall block diagram which shows an automated cell culturing and harvesting device according to a preferred embodiment of the present invention.

FIG. 1 comprises a tubing system 1 which allows the circulation and flow of cell culture medium within the different components of the device; a cell culture chamber in which cells are seeded, grown and detached, which allows the input of cells by the operator through an inlet port (input); an external fresh cell culture medium reservoir 2; an internal buffer cell culture medium reservoir 3; an external cell detaching agent reservoir 7; a gas mixture bottle 6, which is connected to the internal buffer reservoir 3; a waste tank 4; a cell preparation chamber 8 which allows the output of prepared cells by the operator through an outlet port (output); a parameters acquisition system 9 connected to a parameters monitoring system 10.

Cells are injected into the cell culture chamber 5 by means of an inlet port; the cell culture medium flows continuously inside the tubing system 1 from the internal buffer reservoir 3 to the cell culture chamber 5, and circulates back to the same buffer reservoir 3 passing through the parameters control system 9; periodically, under certain parameters values, according to the parameters acquisition system 9 and monitoring system 10, a determined amount of fresh cell culture medium from the external fresh medium reservoir 2 is imported to the internal buffer medium reservoir 3, while a same amount is discharged to the waste tank 4; at the end of the cell culture, a determined amount of cell detaching agent is imported from the external cell detaching agent reservoir 7 into the cell culture chamber 5; after a determined time necessary for cell detaching operation, the detached cells are exported to the cell preparation chamber 8; where, while the excess of detaching agent is discharged to the waste tank 4, the desired volume of prepared cells can be exported through an outlet port.

Figure 2:
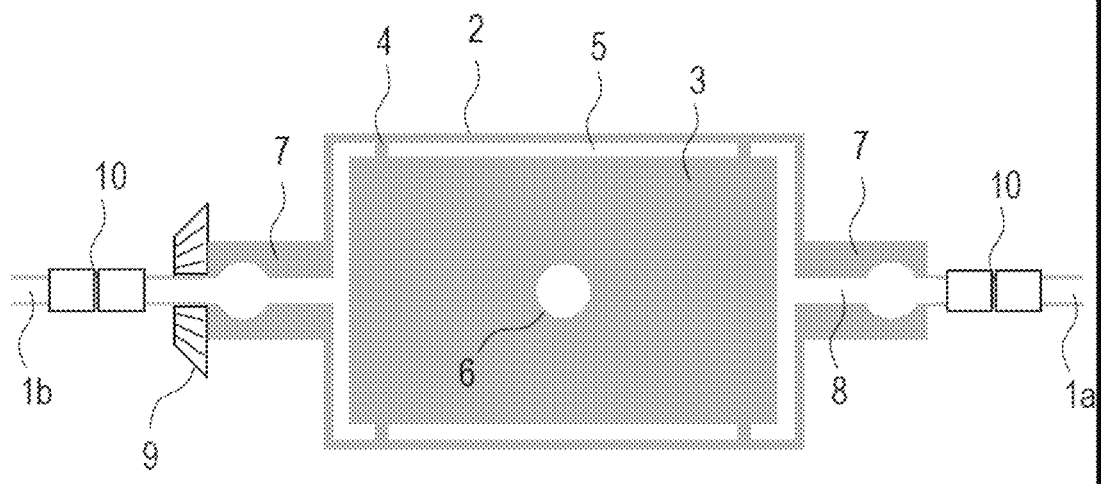
FIG. 2 represents a 4-layer culture chamber (A: top view; B: longitudinal cross-section view).
Figure 2:
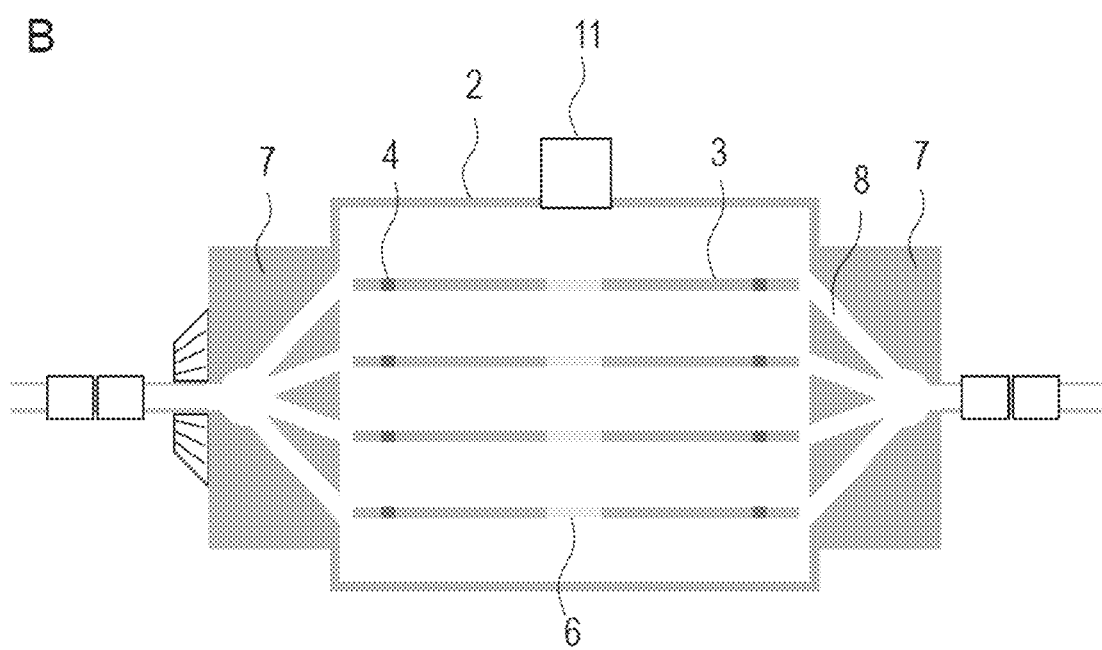

FIG. 2 represent the cell culture chamber which is connected to the tubing system in order to import cell culture medium 1a from one side of the chamber, and let it flow outside the chamber by the other side 1b. The several layers 3 onto which cells adhere and grow are contained within a shell 2 and connected to it through a number of anchors 4. This determines an empty space 5 which allows a better distribution of cells and medium in subsequent phases of operation. Each layer 3 is made by a flat surface, which has a circular gap 6 at its center. Shell 2, as well as flow deflectors 7, may be composed by any bio-compatible material. Non-exclusive examples of suitable materials are polystyrene (PS), polycarbonate (PC), polyoxy-methylene and the like. Layers 3 may be composed by any bio-compatible material suitable for culturing cells, eventually treated for cell adhesion enhancement. A non-exclusive example of suitable material is polystyrene (PS). Non-exclusive examples of treatment for cell adhesion are oxygen plasma surface treatment, poly-D-lysine treatment, active peptide acrylates treatment. Alternatively, layers may be coated with substances suitable for subsequent cell detaching. A non-exclusive example of coating is alginate gel with or without the addition of focal adhesion plaques components (Arginine-Glycine-Aspartic Acid) or other molecules.

The flow deflectors 7, on both sides of the chamber, are made up by a number of pipes (one pipe 8 per layer) in order to divide the incoming cell culture medium flow 1a and the outgoing cell culture medium flow 1b, and to provide accurate distribution of medium to each layer 3. A syringe plug 11, on the top of the chamber, placed above the series of circular gaps 6, allows the initial injection of cells to be seeded onto the layers. Cells may be injected by means of a syringe needle or any other mean suitable to be connected to the plug and to penetrate into the chamber in sterile conditions. The presence of circular gaps allow the syringe needle (or any other suitable mean) to reach not only the upper layer, but also the most internal spaces of the chamber, in order to ensure a more homogeneous distribution of cells during seeding phase.

Following injection of cells inside the chamber, seeding phase consists in mild rotation of the whole culture chamber, by means of a rotation gear 9 coupled with an actuator motor for rotation. Rotation ensures an even more accurate distribution of cells, also thanks to the presence of the empty spaces 5 between the shell and the layers, which allow circulation of medium and cells along the internal walls of the chamber during rotation. The tubing system supports the rotation of the chamber since free rotating joints 10 are present on both sides of the chamber. Mild rotation may occur for a brief, determined time just after injection, and also for brief, determined times in later moments of seeding phase, which lasts up to 24 hours. During this time, cells would adhere on both upper and lower surfaces of the layers. After seeding phase, flow of cell culture medium, together with rotation of the chamber, allows the flow of non-adherent cells outside the chamber.

Figure 3:
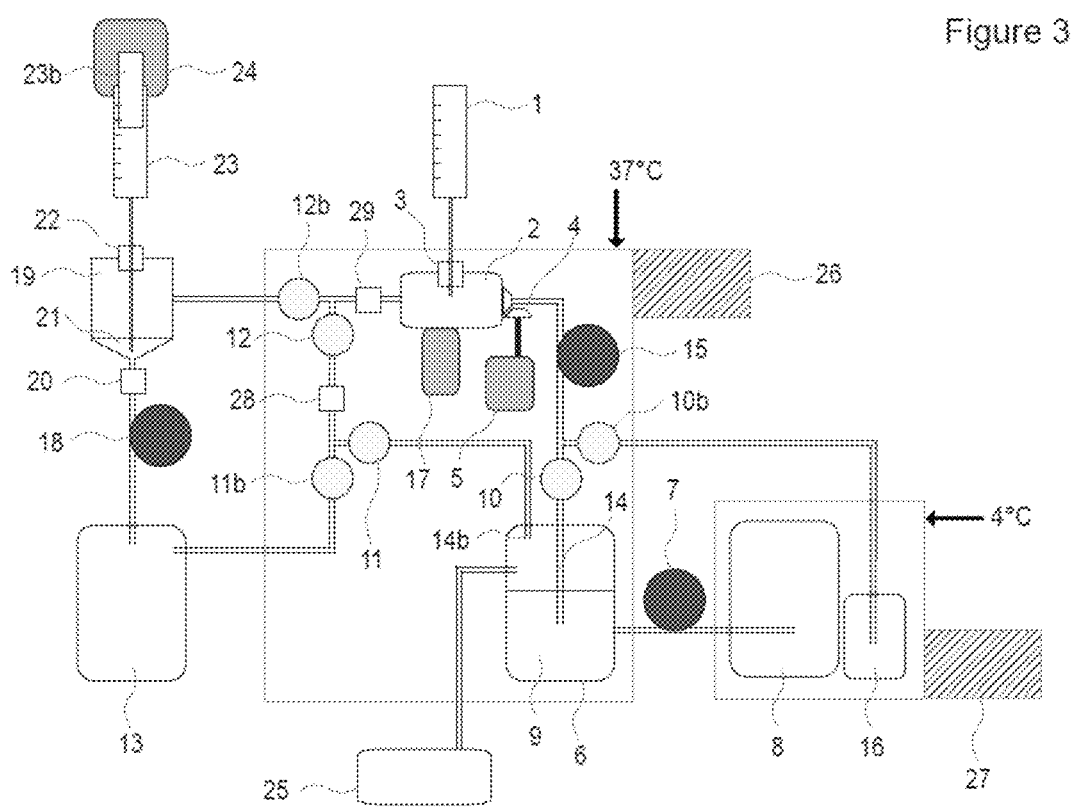
FIG. 3 represents a detailed diagram showing main components of an automated cell culturing and harvesting device according to a preferred embodiment of the present invention.

FIG. 3 represents a cell culturing and harvesting device wherein the operation starts with the injection of cells by means of a syringe 1, or any other suitable mean, into the cell culture chamber 2, passing through a plug 3. In a non-exclusive example, the plug may consist in a silicon septum, or any other mean that ensures sterility during injection. Seeding consists in several, brief, mild rotations of the cell culture chamber 2, made possible by the gear system for rotation 4 and its actuator motor 5, and several, long intervals of time during which the chamber stays static, with its layers in horizontal position. During seeding phase, there is no flow of medium throughout the cell culture chamber. Non-exclusive example of seeding phase total time are 6 to 24 hours. Non-exclusive examples of number of rotations to be actuated during seeding phase are 1 to 12. Non exclusive examples of duration time of each rotation are 1 to 5 minutes. The above described operation may be referred as "seeding phase".

The tubing system 14 connects the internal cell culture medium buffer reservoir 6 to the cell culture chamber 2 and to other components of the device, carrying the cell culture medium which is driven by the action of a peristaltic pump 15 or any other mean. The tubing system may be made by any suitable bio-compatible material.

Non-exclusive examples of bio-compatible tubing materials are silicone, polyvinyl-chloride (PVC), Pharmed® BPT. Reservoir bottle 6 is also connected to gas mixture bottle 25 in order to provide gas exchange with the cell culture medium, as well as maintaining of pH in case of carbonate buffer present within cell culture medium. In this example, 10b, 11b and 12b are normally-closed valves (in example, electro-valves), while 10, 11 and 12 are normally-open valves (in example, electro-valves).

As a consequence of the valves configuration described above, the action of the pump 15 drives the cell culture medium 9 from the reservoir bottle 6 to the cell culture chamber 2, and back to the reservoir bottle 6 through the 14b tubing part. The above described flow of culture medium may be referred as "circulation phase".

Following seeding phase, mobilization of medium throughout the cell culture chamber would ensure removal of non adherent cells and change of the cell culture medium inside the cell culture chamber. By closing the normally-open valve 11 and opening the normally-closed valve 11b, the medium will flow from the cell culture chamber to the waste tank 13. The above described flow of culture medium may be referred as "washing phase", and may utilize a certain amount of buffered cell culture medium.

Following washing phase, the amount of cell culture medium which has been discharged to the waste tank 13 should be replaced by the same amount of fresh cell culture medium. To this end, the action of the pump 7 (or any other suitable mean) and a tubing system connecting the reservoir bottle 6 and the external fresh medium reservoir 8, ensure the import of fresh medium into the reservoir bottle. The above described flow of fresh culture medium may be referred as "refill phase".

The growth (otherwise indicated as "expansion") of adherent cells inside the cell culture chamber lasts for the time necessary to obtain the desired number of cells, i.e. for the time necessary to obtain the maximum number of cells available for the layers surface. During cell growth, circulation phase is alternated with several washing phases and refill phases. The number of washing phases and refill phases, as well as their timing, depend on the value of several parameters characterizing the circulating cell culture medium. Several parameters sensors (28 and 29 in the present embodiment) may be used in order to monitor, record and control the composition of the circulating culture medium. According to sensors data, which are set at certain parameters values and certain thresholds, circulating phase may be followed by washing and refill phase, in order to recovery appropriate composition of the circulating culture medium. This operation is automatically controlled by parameters control unit, which automatically acts on valves 11, 11b and pump 7 as above described. Non-exclusive examples of parameters to be monitored, recorded and controlled are pH, glucose concentration, dissolved oxygen concentration, lactic acid concentration. In particular, in a non-exclusive example, glucose consumption rate may be derived from glucose concentration dynamics during cell growth phase, and used as an indirect indicator of cell concentration inside the chamber. Thus, the end of cell growth phase may be automatically decided by the device.

Following appropriate cell growth, as described above, detaching of adherent cells grown onto layers inside the chamber, is necessary. To this aim, by closing the valves 10 and 11 and by opening valve 11b (while valves 10b and 12b rest closed), the action of pump 15 will result in emptying the culture chamber, since cell culture medium will be driven to waste tank 13. The above described discard of culture medium may be referred as "emptying phase".

Once cell culture chamber is empty (i.e. no cell culture medium is present inside), valve 10b is open (while valve 10 rests closed, as described above), in order to allow pump 15 to let a certain amount of detaching agent 16 flow inside the cell culture chamber. The amount of detaching agent is pre-determined and is sufficient to fill the cell culture chamber. Non-exclusive examples of detaching agents are: citrate (when cell culture layers are coated with alginate gel), trypsin/EDTA, collagenase (when cells adhere onto plastic).

Together with the detaching effect of the detaching agent on the adherent cells, in order to improve detaching efficiency, fast rotation of cell culture chamber may be carried out. As described above, rotation is done by gear system for rotation 4 and its actuator motor 5. In addition, in order to further improve cell detaching efficiency, cell culture chamber may be subjected to vibration movements, actuated by vibration motor 17. A non-exclusive example of vibration timing is approximately 30 seconds, while vibration intensity is 0.1 to 10 Hertz. The above described detaching of cells may be referred as "detaching phase".

After detaching of cells, valve 12 is closed, while valve 12b is open; by doing so, pump 15 will let flow detached cells, together with detaching agent, outside the cell culture chamber, to reach cell preparation chamber 19. Cell preparation chamber is provided with a filter 20 at its conical bottom. Pores of this filter are designed in order to allow passing of detaching agent and any other liquid substance, while blocking cells. A non-exclusive example of pores dimension of filter 20 is 1 micrometer. Once cell preparation chamber is filled with detached cells and detaching agent, pump 18 would let liquid flow through filter 20 towards waste tank 13, while leaving concentrated cells 21 at the conical bottom of preparation chamber.

The above described concentration of cells and discard of detaching agent may be referred as "preparation phase".

In order to harvest the concentrated cells, a syringe 23 (or any other suitable mean) may be connected to a plug 22. In a non-exclusive example, the plug may consist in a silicon septum, or any other mean that ensures sterility during injection. Syringe piston 23b may be attached to piston actuator motor 24. Actuator motor pulls piston up in order to fill syringe with detached concentrated cells. In a non-exclusive example, actuator motor may also pull piston up and down several times in order to ensure homogeneous re-suspension of concentrated cells. Syringe may also contain one or more appropriate substances such as diluting agents, preserving agents, carrier agents. Non-exclusive examples of these substances are hyaluronic acid solution, physiologic solution, saline buffer solution, collagene solution, platelet-rich plasma (PRP). The above described final harvesting of cells from cell preparation chamber may be referred as "harvesting phase".

The syringe 23 (or any other suitable mean), containing harvested cells and eventually other diluting agent as described above, may be removed and used to implant cells directly into the body. Non-exclusive examples of implant sites are articulations, mammary tissue, heart, liver, cerebro spinal fluid (CSF), blood.

All the described components comprising cell culture chamber 2, buffer medium reservoir 6, tubing system 14 and related components are contained within a compartment (as shown in FIG. 3) which is subjected to temperature control, by an appropriate temperature control system 26. Optimal temperature for seeding and expansion of cells is 37° C. Gas exchange bottle 25, waste tank 13, cell preparation chamber 19 and related components may be not subjected to temperature control, and may function at room-temperature. External fresh medium reservoir 8 and detaching agent 16 are contained within a separated compartment (as shown in FIG. 3) which is subjected to temperature control, by an appropriate temperature control system 27.

Medium reservoir and detaching agent maintained at a temperature between about 4° C. and about 8° C.

With reference to FIG. 3, components constituting the disposable "cartridge" system are: 2, 3, 6, 14, 19, 20, 22, 23, 23b. Components 8, 13 and 16 are also disposable, and are appropriately connected to the "cartridge" system by means of tubing system.

The invention claimed is:
1. An automated cell culturing and harvesting device, which expands, detaches and prepares cells, ready to be implanted in vivo, the device comprising a disposable cartridge comprising the following components:
   a) a disposable tubing system allowing the circulation and flow of cell culture medium within the different components of the device;
   b) a disposable cell culture chamber configured for input of cells by an operator through an inlet port thereby allowing the seeding, growing and detaching of the cells all within the cell culture chamber;
   c) a disposable external fresh cell culture medium reservoir;
   d) a disposable internal buffer cell culture medium reservoir;
   e) a disposable external cell detaching agent reservoir;
   f) a gas mixture bottle connected to the disposable internal buffer culture medium reservoir; and
   g) a disposable cell preparation chamber allowing the output of prepared cells by the operator through an outlet port;
   thereby providing a disposable cartridge configured for insertion into the device and to minimize contamination of the prepared cells;
   wherein the cell culture chamber is coupled to a vibration motor configured to transmit vibrations in Hertz to the cell culture chamber to facilitate detachment of the cells after cell detaching agent is pumped into the cell culture chamber, wherein the cell culture chamber is rotated to allow harvesting of the detached cells, and wherein the cell preparation chamber is configured to receive the detached cells.

2. The automated cell culturing and harvesting device according to claim 1, wherein the device comprises two separated temperature controlled compartments which are adjusted at different temperatures by a temperature control system.

3. The automated cell culturing and harvesting device according to claim 2, wherein the first compartment is subjected to temperature control in order to maintain a temperature of about 37° C. and includes the cell culture chamber and a certain amount of circulating cell culture medium; and the second compartment is subjected to temperature control in order to maintain a temperature between about 4° C. and about 8° C. and includes a fresh medium reservoir, and a cell detaching agent.

4. The automated cell culturing and harvesting device according to claim 1, wherein the tubing system is configured for a continuous flow of medium between the internal cell culture medium reservoir and the cell culture chamber, wherein the cell culture chamber is provided with a continuous circulation of medium.

5. The automated cell culturing device according to claim 3, wherein the tubing system is configured for an input of fresh medium from the second compartment of said device, and medium discharge to a waste tank.

6. The automated cell culturing and harvesting device according to claim 1, wherein the culture chamber includes comprises several growth surfaces arranged in layers.

7. The automated cell culturing and harvesting device according to claim 6, wherein the cell culture chamber further comprises flow deflectors, and wherein the cell culture chamber, the external shell and the flow deflectors are composed of a bio-compatible material selected from the group consisting of polystyrene (PS), polycarbonate (PC), and polyoxymethylene, and the growth surface layers are composed by polystyrene (PS) treated for cell adhesion enhancement.

8. The automated cell culturing and harvesting device according to claim 7, wherein the treatments for cell adhesion comprise: oxygen plasma surface treatment, poly-D-lysine treatment, active peptide acrylates treatment, or layers coated with alginate gel with or without the addition of adhesion focal plaques components (RGD) or molecules.

9. The automated cell culturing and harvesting device according to claim 1, wherein administration of a detaching agent is coupled to rotation and vibration of the cell culture chamber respectively by an actuator motor and the vibration motor.

10. The automated cell culturing and harvesting device according to claim 1, wherein the cell preparation chamber is connected to a syringe or other extraction devices for immediate collection of cells.

11. The automated cell culturing and harvesting device according to claim 1, wherein the cells to be seeded, expanded, prepared and harvested are non-embryonic stem non-germ cells.

12. The automated cell culturing device and harvesting according to claim 1, wherein cells to be injected into the cell culture chamber are adherent proliferative cells.

13. The automated cell culturing and harvesting device according to claim 11, wherein the non-embryonic stem non-germ cells are bone marrow, adipose tissue, umbilical cord blood, umbilical cord matrix, peripheral blood, placenta, placental blood, muscle, brain, kidney and other solid organs or excreted fluids.

14. The automated cell culturing and harvesting device according to claim 12, wherein the cells to be injected are adipose-derived mesenchymal stem cells (AD-MSC) or bone marrow derived mesenchymal stem cells (BMSC).

15. The automated cell culturing and harvesting device according to claim 1, further comprising at least one sensor configured to monitor pre-set parameters within the tubing system and the cell culture chamber, and configured to send parameter data to a parameters acquisition system, wherein the parameters acquisition system is connected to a parameters monitoring system, the parameters monitoring system being configured to automatically control at least one pump based on parameter data received from the parameters acquisition system, thereby automating operation of the device.

16. The automated cell culturing and harvesting device according to claim 1, wherein the cell preparation chamber is adapted with a filter configured to allow passage of the cell detaching agent but blocks passage of the harvested, detached cells.

17. The automated cell culturing and harvesting device according to claim 1, wherein the vibration motor is configured to transmit vibrations from 0.1 to 10 Hertz.

18. A method for expanding and preparing mesenchymal stem cells for in vivo cell therapy in mammals, the method comprising:

providing an automated cell culturing and harvesting device according to claim 1;

a) providing the device with fresh cell culture medium;

b) seeding the disposable cell culture chamber of the device with cells;

c) growing the cells for a sufficient amount of time; and d) harvesting the grown cells.

19. The method of according to claim 18, wherein the cells for seeding into the disposable cell culture chamber are cells for immunomodulation or cells for tissue repair.

* * * * *